United States Patent [19]

Treuner et al.

[11] 4,169,947

[45] Oct. 2, 1979

[54] 7β-[[[2-ACYLAMINO]-1,2-DIOXOETHYL-]AMINO]ACYL CEPHALOSPORINS

[75] Inventors: Uwe D. Treuner; Hermann Breuer, both of Regensburg, Fed. Rep. of Germany

[73] Assignee: E. R. Squibb & Sons, Inc., Princeton, N.J.

[21] Appl. No.: 910,548

[22] Filed: May 30, 1978

[51] Int. Cl.² .................. C07D 501/36; C07D 501/34; C07D 501/46; C07D 501/22

[52] U.S. Cl. ......................................... 544/27; 544/4; 544/21; 544/22; 544/24; 544/25; 544/26; 544/28; 544/30

[58] Field of Search ...................... 544/21, 22, 24, 25, 544/26, 27, 28, 30, 4

[56] References Cited

U.S. PATENT DOCUMENTS

| 4,096,330 | 6/1978 | Treuner et al. ................... 544/26 |
| 4,113,943 | 9/1978 | Treuner et al. ................... 544/26 |

Primary Examiner—David Wheeler
Attorney, Agent, or Firm—Lawrence S. Levinson

[57] ABSTRACT

7β-[[[2-Acylamino]-1,2-dioxoethyl]amino]acyl cephalosporins of the formula

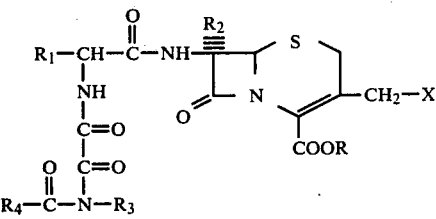

wherein R is hydrogen, lower alkyl, phenyl-lower alkyl, diphenyl-lower alkyl, tri(lower alkyl)silyl, trihaloethyl or a salt forming ion; $R_1$ is hydrogen, lower alkyl, saturated or unsaturated cycloalkyl, phenyl, phenyl-lower alkyl, substituted phenyl or certain heterocyclic groups; $R_2$ is hydrogen or methoxy; $R_3$ is hydrogen, lower alkyl or phenyl-lower alkyl; $R_4$ is lower alkyl, cycloalkyl, phenyl, substituted phenyl or certain heterocyclic groups; and X is hydrogen, lower alkanoyloxy, carbamoyloxy, lower alkoxy, lower alkylthio,

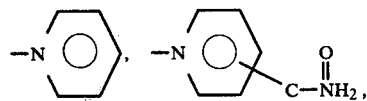

or certain heterothio groups, are useful as antibacterial agents.

10 Claims, No Drawings

7β-[[[2-ACYLAMINO]-1,2-DIOXOETHYL-]AMINO]ACYL CEPHALOSPORINS

SUMMARY OF THE INVENTION

Cephalosporins and penicillins having various acyl side chain are typified, for example, in U.S. Pat. Nos. 3,573,294, 3,997,533, 4,028,354, 4,073,783 and 4,009,272.

7β-(2-Amino-1,2-dioxoethyl)amino]acyl cephalosporins are described in our copending application Ser. No. 776,400, filed Mar. 10, 1977.

This invention relates to new 7β-[(2-amino-1,2-dioxoethyl)amino]acyl cephalosporin derivatives of the formula

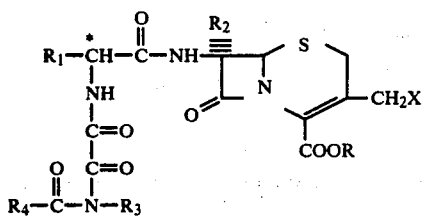

which are distinguishable from such prior known compounds.

R represents hydrogen, lower alkyl, phenyl-lower alkyl, diphenyl-lower alkyl, tri(lower alkyl)-silyl, trihaloethyl or a salt forming ion.

$R_1$ represents hydrogen, lower alkyl, saturated or unsaturated cycloalkyl, phenyl, phenyl-lower alkyl, substituted phenyl or certain heterocyclic groups.

$R_2$ represents hydrogen or methoxy. The $R_2$ substituent is in the α-configuration as indicated by the broken lines.

$R_3$ represents hydrogen, lower alkyl or phenyl-lower alkyl; $R_4$ represents lower alkyl, cycloalkyl, phenyl, substituted phenyl or certain heterocyclic groups.

X represents hydrogen, lower alkanoyloxy, carbamoyloxy, lower alkoxy, lower alkylthio, certain heterothio groups,

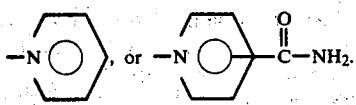

When X is pyridinium or carbamoyl substituted pyridinium, the compounds can be structurally represented as having the formula

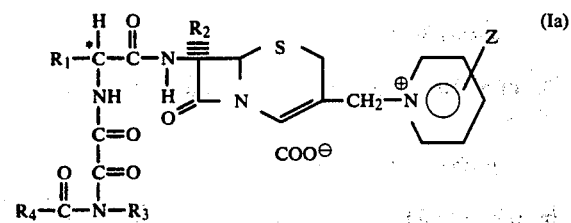

wherein Z is hydrogen or carbamoyl.

The asterisk indicates an asymmetric carbon atom.

DETAILED DESCRIPTION OF THE INVENTION

The various groups represented by the symbols have the meaning defined below and these definitions are retained throughout this specification.

The lower alkyl groups referred to throughout this specification include straight or branched chain hydrocarbon groups containing 1 to 7 carbon atoms, preferably 1 to 4 carbons. Examples of the type of groups contemplated are methyl, ethyl, propyl, isopropyl, butyl, t-butyl, etc. The lower alkoxy and lower alkylthio groups include such lower alkyl groups attached to an oxygen or sulfur, respectively, e.g. methoxy, ethoxy, propoxy, methylthio, ethylthio, propylthio, etc. The phenyl-lower alkyl and diphenyl-lower alkyl groups include such lower alkyl groups attached to one or two phenyl rings, preferably benzyl, phenethyl and diphenylmethyl.

The saturated and unsaturated cycloalkyl groups are the alicyclic groups having up to 7 carbons and up to 2 double bonds in the ring, i.e., the cycloalkyl groups cyclopropyl, cyclobutyl, cyclopentyl, cyclohexyl and cycloheptyl, the cycloalkenyl groups having up to 7 carbons with one double bond, cyclobutenyl, cyclopentenyl, cyclohexenyl and cycloheptenyl and the cycloalkadienyl groups having up to 7 carbons with two double bonds located at various positions such as 1,4-cyclohexadienyl (which is preferred).

The substituted phenyl groups include one or two substituents selected from halogen (preferably chlorine or bromine), lower alkyl (preferably having 1 to 4 carbons, especially methyl or ethyl), lower alkoxy (preferably having 1 to 4 carbons, especially methoxy or ethoxy), and hydroxy, e.g., 2-, 3-, or 4-chlorophenyl, 2-, 3-, or 4-bromophenyl, 2-, 3-, or 4-hydroxyphenyl, 3,5-dichlorophenyl, 2-, 3-, or 4-methylphenyl, 2-, 3- or 4-ethoxyphenyl, etc.

The salt forming ions represented by R are metal ions, e.g., aluminum, alkali metal ions such as sodium or potassium, alkaline earth metal ions such as calcium or magnesium, or an amine salt ion, of which a number are known for this purpose, for example, phenyl-lower alkylamines such as dibenzylamine, N,N-dibenzylethylenediamine, lower alkylamines such as methylamine, triethylamine, and N-lower alkylpiperidines such as N-ethylpiperidine. Sodium and potassium are the preferred salt forming ions.

The halogens are the four common halogens, of which chlorine and bromine are preferred. In the case of the trihaloethyl group represented by R, 2,2,2-trichloroethyl is preferred.

Trimethylsilyl is the preferred tri(lower alkyl)-silyl group.

The heterocyclic groups represented by $R_1$ are 2-thienyl, 3-thienyl, 2-furyl, 3-furyl, 2-pyridyl, 3-pyridyl, 4-pyridyl, or 2-aminothiazol-4-yl.

The heterocyclic groups represented by $R_4$ are the thienyl, furyl and pyridyl groups represented by $R_1$, thiazolyl and isothiazolyl, i.e. the groups,

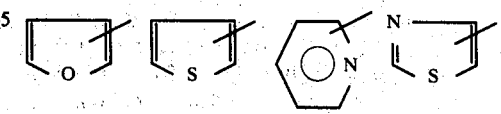

-continued

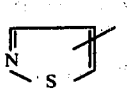

Lower alkanoyloxy refers to a group of the formula

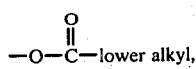

preferably wherein the lower alkyl group is methyl.

The heterothio groups represented by X are

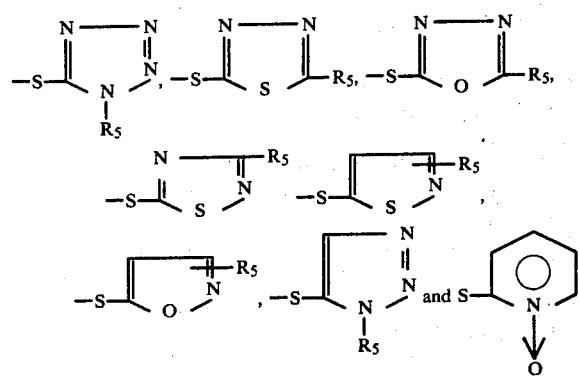

wherein $R_5$ is hydrogen or lower alkyl (preferably having 1 to 4 carbons, especially methyl or ethyl).

The products of this invention are produced by acylating a cephem compound having the formula

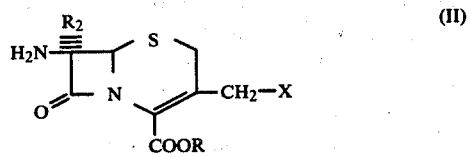

with an acid having the formula

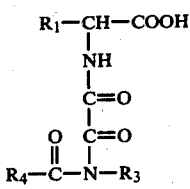

or an activated derivative like the acid halide, activated ester like the nitrophenyl ester, dinitrophenyl ester, diphenylmethyl ester, or mixed anhydride, and/or in the presence of a coupling agent like dicyclohexlcarbodiimide.

The compound of formula II is preferably in the form of an ester, i.e, R is an easily removable group like diphenylmethyl, which is preferred, t-butyl, trimethylsilyl, etc.

One preferred synthesis comprises reacting the acid of formula II with the diphenylmethyl ester of the compound of formula II in the presence of dicyclohexylcarbodiimide and then hydrolyzing the ester with trifluoroacetic acid and anisole to obtain the free carboxyl group in the 4-position. A salt can be obtained from the acid by reaction with the base having the desired cation.

This reaction can be carried out, for example, by dissolving or suspending the acid in an inert organic solvent such as chloroform, tetrahydrofuran, methylene chloride, dioxane, benzene or the like, and adding, at a reduced temperature of about 0°-5° C., about an equimolar amount of the compound of formula II in the presence of a coupling agent such as dicyclohexylcarbodiimide. The product of the reaction is then isolated by conventional procedures, e.g., by concentration or evaporation of the solvent. If a derivative such as the diphenylmethyl ester is used, the free acid is obtained by hydrolysis, e.g., with trifluoroacetic acid and anisole or the like. Salts can then be derived from the free acid.

According to another embodiment, a compound of the formula

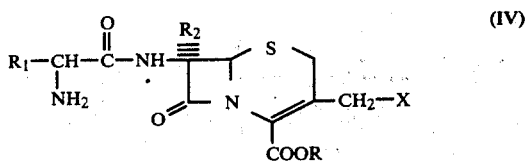

is made to react with an acyl halide of the formula

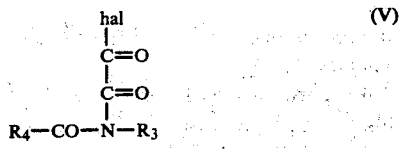

wherein hal represents halogen, preferably chlorine, or with a nitrophenyl ester of the formula

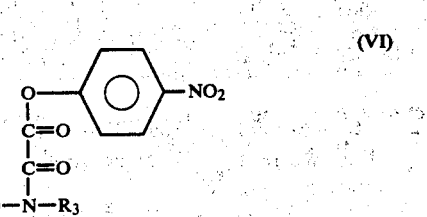

The compounds of formula I wherein X is pyridinium or carbamoyl substituted pyridinium can be prepared by reacting a compound of formula I wherein X is acetoxy with pyridine or carbamoyl substituted pyridine in a polar solvent such as water and in the presence of a catalyst such as an alkali metal thiocyanate by the method described in U.S. Pat. No. 3,792,047 and German Offenlegungsschrift No. 2,234,280.

Compounds of formula I wherein X is a heterothio group can also be produced by reacting a compound of formula I wherein X is acetoxy with a mercaptan of the formula

or an alkali metal (preferably sodium) salt of the formula

by the methods described in U.S. Pat. Nos. 3,855,213; 3,890,309; and 3,892,737.

The starting material of formula III can be produced from an α-amino acid ester having the formula $$R_1-CH-COOY \quad (VIII)$$
$$| \quad NH_2$$

wherein $R_1$ has the same meaning as defined above and Y is a readily removable group, e.g., diphenylmethyl, nitrophenyl, dinitrophenyl, t-butyl, trimethylsilyl or the like, which is made to react with an oxalic acid halide or nitrophenyl ester of formulas V and VI, respectively.

Activated derivatives of the acids of formula III are produced by reaction with thionyl chloride, esterifying agent, anhydride, or the like, by conventional procedures.

Alternatively, an α-amino acid ester of formula VIII, preferably the diphenylmethyl ester, nitrophenyl ester or dinitrophenyl ester, is made to react with an oxalyl halide like oxalyl chloride to obtain a compound of the formula $$R_1-CH-COOY \quad (IX)$$
$$| \quad NH$$
$$| \quad C=O$$
$$| \quad C=O$$
$$| \quad hal$$

wherein hal represents halogen, preferably chlorine, and Y is one of the foregoing ester groups like diphenyl methyl, p-nitrophenyl or 2,4-dinitrophenyl. Reaction of this derivative with a compound of the formula $$R_4-CO-N-Si(CH_3)_3 \quad (X)$$

(which is formed from the amide $R_4-CO-NH_2$, triethylamine and a silylating agent like trimethylsilyl chloride, monotrimethylsilyltrifluoroacetamide or bis trimethylsilylacetamide) yields a product of the formula $$R_1-CH-COOY \quad (XI)$$
$$| \quad NH$$
$$| \quad C=O$$
$$| \quad C=O$$
$$| \quad R_4-CO-N-R_3$$

When Y is nitrophenyl or dinitrophenyl, the intermediate of formula XI can be made to react with the compound of formula II.

When Y is diphenylmethyl in formula XI it is preferable to react this intermediate with an acid, e.g., hydrochloric acid in glacial acetic acid, to form a compound of the formula $$R_1-CH-COOH \quad (XII)$$
$$| \quad NH$$
$$| \quad C=O$$
$$| \quad C=O$$
$$| \quad R_4-CO-N-R_3$$

which is then made to react with the compound of formula II, preferably in the form of its diphenylmethyl ester, the ester group then being removed as described.

The carboxylate salts of the compound of formula I are formed by reacting the carboxyl group of the cephalosporanic acid moiety, i.e., R is hydrogen, with any of the salt forming ions described above.

It will be appreciated that the compounds of formula I are optically active due to the presence of an asymmetric carbon atom indicated by the asterisk. By selection of the appropriate starting material it is possible to obtain the compounds of formula I as a mixture of optically active isomers or isolated as a single isomer. The various isomers as well as their mixtures are within the scope of this invention.

Preferred compounds of this invention are the acids and alkali metal salts of formula I (i.e. R is hydrogen, sodium or potassium) wherein X is acetoxy or heterothio, especially 1-methyl-1H-tetrazol-5-ylthio; $R_1$ is phenyl or a heterocyclic selected from 2-thienyl, 3-thienyl, 2-furyl or 3-furyl, especially 2-furyl and 2-thienyl; $R_2$ is hydrogen or methoxy, especially hydrogen; $R_3$ is hydrogen or lower alkyl, especially hydrogen; and $R_4$ is lower alkyl or furyl, especially 2-furyl.

The most preferred final compounds are the acids and alkali metal salts of formula I wherein $R_1$ is 2-thienyl or 2-furyl; $R_2$ and $R_3$ each is hydrogen; $R_4$ is 2-furyl; and X is heterothio particularly wherein X is

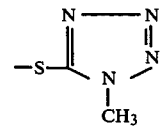

The acid compounds of formula I have a broad spectrum of antibacterial activity against both gram positive and gram negative organisms such as *Staphylococcus aureus, Salmonella typhimurium, Citrobacter freundii, Shigella sonnei, Proteus mirabilis, Proteus rettgeri, Escherichia coli, Enterobacter cloacae, Klebsiella pneumoniae, Klebsiella, aerogenes*, etc. They may be used as antibacterial agents to combat infections due to organisms such as those named above, and in general may be utilized in a manner similar to cephradine and other cephalosporins. For example, a compound of formula I or a physiologically acceptable salt thereof may be used in various animal species in an amount of about 15 to 100 mg/kg., daily, orally or parenterally, in single or two to four divided doses to treat infections of bacterial origin, e.g., at about 20 mg/kg. in mice.

About 50 to 600 mg. of an acid compound of formula I or a physiologically acceptable salt thereof may be incorporated in an oral dosage form such as tablet, capsule or elixir or in an injectable form in a sterile aqueous vehicle prepared according to conventional pharmaceutical practice.

Illustrative process details are provided in the examples. All temperatures are in degrees celsius.

EXAMPLE 1

[(2-Furanylcarbonyl)amino]oxoacetyl chloride 3.6 g. of N-(trimethylsilyl)-2-furancarboxamide are dissolved in 50 ml. of absolute methylene chloride and the solution is added dropwise at −10° to a solution of 1.8 g. of oxalyl chloride in 100 ml. of methylene chloride. The mixture is stirred for one hour at 0°. After evaporating the solvent, [(2-Furanylcarbonyl)amino]oxoacetyl chloride remains as a yellowish oil which is used for the next reaction without further purification.

EXAMPLE 2

[(2-Furanylcarbonyl)amino]oxoacetic acid, 4-nitrophenyl ester 2.7 g. of nitrophenyl and 2.6 g. of dimethylaniline are dissolved in 50 ml. of methylene chloride and a solution of 4.02 g. of [(2-furanylcarbonyl)amino]oxoacetyl chloride in methylene chloride is added dropwise at 0°. After stirring for two hours, the reaction mixture is extracted once with dilute hydrochloric acid and once with 50 ml. of water. The organic phase is dried and concentrated yielding 3.2 g. of [(2-Furanylcarbonyl)amino]oxoacetic acid, 4-nitrophenyl ester, which is recrystallized from toluene to give 2.6 g. of light beige crystals, m.p. 115°.

EXAMPLE 3

(6R-trans)-7-[[D-[[[(2-Furanylcarbonyl)amino]oxoacetyl]amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid, monohydrate 2.86 g. of 7-[D-[2-amino-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid, trifluoroacetate are suspended in 100 ml. of absolute acetonitrile. After the addition of 3 g. of bistrimethylsilylacetamide, the mixture is stirred until a clear solution results. This is cooled to 0°, 0.7 g. of N-methylmorpholine and a small granule of 4-dimethylaminopyridine are added and a solution of 1.1 g. of [(2-furanylcarbonyl)amino]oxoacetyl chloride in 15 ml. of methylene chloride is added dropwise. After one hour, 15 ml. of methanol are added and the mixture is stirred for 30 minutes more. The solvent is distilled off leaving a brown oil which is stirred with 200 ml. of water, 300 ml. of ethyl acetate and 10 ml. of 2 N hydrochloric acid for 30 minutes. The organic phase is washed with water, treated with charcoal, dried and concentrated. 2.2 g. of crude (6R-trans)-7-[[D-[[[(2-Furanylcarbonyl)amino]oxoacetyl]amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid, monohydrate are obtained. The crude product is purified by precipitation from tetrahydrofuran ether to obtain a beige powder, m.p. 156° (dec.)

EXAMPLE 4

(6R-trans)-7-[[DL-[[[(2-Furanylcarbonyl)amino]oxoacetyl]-amino]-2-furylacetyl]amino]-3-[[(1-methyl-1H-tetrazol-5-yl)thio]methyl]-8-oxo-5-thia-1-azabicyclo[4.2.0]oct-2-ene-2-carboxylic acid 7-[DL-[2-amino-2-furanylacetyl]amino]-3-[[(1-methyl-1H-tetrazol-5-yl)thio]methyl]-8-oxo-5-thia-1-azabicyclo[4.2.0]oct-2-ene-2-carboxylic acid, trifluoroacetate is substituted for the 7[-D-[2-amino-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid, trifluoroacetate, in the procedure of Example 3 to obtain (6R-trans)-7-[[DL-[[[(2-Furanylcarbonyl)amino]oxoacetyl]-amino]-2-furylacetyl]amino-3-[[(1-methyl-1H-tetrazol-5-yl)thio]methyl]-8-oxo-5-thia-1-azabicyclo[4.2.0]oct-2-ene-2-carboxylic acid as a beige powder, m.p. 144° (dec.).

The sodium salt is obtained by freeze drying an equimolar aqueous solution of the above acid and sodium bicarbonate.

EXAMPLE 5

D-α-[[[(2-Furanylcarbonyl)amino]oxoacetyl]amino]-2-thiopheneacetic acid, diphenylmethyl ester 3.83 g. of D-2-thienylglycine, diphenylmethyl ester and 1.25 g. of dimethylaniline are dissolved in 50 ml. of methylene chloride. 1.1 g. of [(2-furanylcarbonyl)amino]oxoacetyl chloride in 20 ml. of methylene chloride are added dropwise at 0°. After one hour, the mixture is extracted with water, and the organic phase is dried and concentrated to obtain D-α-[[[(2-Furanylcarbonyl)amino]oxoacetyl]amino]-2-thiopheneacetic acid, diphenylmethyl ester as white crystals which are recrystallized from carbon tetrachloride, m.p. 76°-80°.

EXAMPLE 6

Alternative preparation of (6R-trans)-7-[[D-[[[(2-Furanylcarbonyl)amino]oxoacetyl]-amino]-2-thienylacetyl]amino-3-[[(1-methyl-1H-tetrazol-5-yl)thio]methyl]-8-oxo-5-thia-1-azabicyclo[4.2.0]oct-2-ene-2-carboxylic acid, monohydrate.

2.86 g. of 7-[D-[2-amino-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid, trifluoroacetate are dissolved with 3 g. of bistrimethylsilylacetamide in 50 ml. of dimethylacetamide. 1 g. of N-hydroxy benzotriazole and [(2-furanylcarbonyl)amino]oxoacetic acid 4-nitrophenyl ester are added and the mixture is stirred for 4 hours at 5°. 300 ml. of water are added with stirring, the mixture is acidified with 2 N hydrochloric acid and then extracted three times with 100 ml. portions of ethyl acetate. The washed organic phase is treated with charcoal and concentrated to leave 2.3 g. of crude (6R-trans)-7-[[D-[[[(2-Furanylcarbonyl)amino]oxoacetyl]-amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid, monohydrate as a brown powder, m.p. 154° (dec.).

EXAMPLE 7

D-α-[[[(2-Furanylcarbonyl)amino]oxoacetyl]amino]-2-thiopheneacetic acid 2 g. of D-α-[[[(2-furanylcarbonyl)amino]oxo-acetyl]amino]-2-thiopheneacetic acid, diphenylmethyl ester are stirred for 10 minutes at 0° with 15 ml. of trifluoroacetic acid. After evaporation of the trifluoroacetic acid, the residue is recrystallized from ethanol to obtain D-α-[[[(2-Furanylcarbonyl)amino]oxo-acetyl]amino-2-thiopheneacetic acid as beige crystals, m.p. 169°.

EXAMPLE 8

7β-Amino-3-[[(1-methyl-1H-tetrazol-5-yl)thio]methyl]-8-oxo-5-thia-1-azabicyclo[4.2.0]oct-2-ene-2-carboxylic acid To a stirred suspension of 27.2 g. 7-aminocephalosporanic acid (0.1 mole) in 150 ml. of acetone and 100 ml. of H₂O at 0°-5° is added 50 ml. of 2 N NaOH, with care being taken to keep the pH below 8.5. A solution of 12.7 g. (0.11 mole) of 1-methyl-5-mercapto-1H-tetrazole in 50 ml. of 2 N NaOH is added, and the mixture is allowed to warm to room temperature. The stirred mixture is then maintained at 60° (internal temperature) under nitrogen for 3 hours at pH 7-7.5 by the periodic addition of dilute aqueous NaOH. The mixture is cooled in an ice-water bath, and while stirring, 3 N HCl is added to adjust the pH to 3.9. Stirring is continued for 15 minutes, and the precipitate is collected by filtration, washed with water, and then acetone, and finally dried to give the desired product as a powder (18.4 g.).

EXAMPLE 9

7β-Amino-3-[[(1-methyl-1H-tetrazol-5-yl)thio]methyl]-8-oxo-5-thia-1-azabicyclo[4.2.0]oct-2-ene-2-carboxylic acid, diphenylmethyl ester A mixture of 16.4 g. (0.05 mole) of the acid product from Example 9, 10.3 g. (0.054 mole) p-toluenesulfonic acid monohydrate, 350 ml. of dioxane (dried by passage through basic alumina), and dry $CH_3OH$ is stirred at room temperature under nitrogen for 30 minutes. The clear solution is evaporated to a residue, and water and $CH_3OH$ are removed by four evaporations of 100 ml. quantities of dioxane. Fresh dioxane (300 ml.) is then added to the residue followed by a solution of crystalline diphenyldiazomethane (19.4 g., 0.10 mole) in 150 ml. of dry dimethoxyethane. The mixture is initially shaken vigorously for 10-15 minutes and then stirred at room temperature for 3 hours. Methanol (25 ml.) is added, and the red solution is stirred until it has turned yellow-orange. The solvents are removed in vacuo, and the residue is treated with 400 ml. of $CH_2Cl_2$ and a solution of 20 g. of $K_2HPO_4$ in 250 ml. of water. The $CH_2Cl_2$ layer is washed with water and saturated NaCl, and finally dried ($MgSO_4$) to give a residue after removal of the solvent in vacuo. Treatment of the residue with $Et_2O$ gives a solid (27 g.). Column chromatography of this solid on silica gel by elution with $CHCl_3$ and then $EtOAc$-$CHCl_3$ (4:1) provides the desired product as a residue (12.9 g.). Treatment with EtOAc then provides 8.0 g. of the desired product as a pale yellow powder.

EXAMPLE 10

7-[[D-[[[(2-Furanylcarbonyl)amino]oxoacetyl]amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid (7.5 mM) of D-α-[[[(2-furanylcarbonyl)amino]oxoacetyl]amino]-2-thiopheneacetic acid are added at −10° to a solution of 2.5 g. (7.5 mM) of 7β-amino-3-[[(1-methyl-1H-tetrazol-5-yl)thio]methyl]-8-oxo-5-thia-1-azabicyclo[4.2.0]oct-2-ene-2-carboxylic acid and 3.7 g. of bistrimethylsilyl acetamide in 100 ml. of acetonitrile. The mixture is stirred for one hour and the solvent is then distilled off. The residue is taken up in 50 ml. of methanol and 1 ml. of 2 N hydrochloric acid, then treated with charcoal. The crude product, 7-[[D-[[(2-furanylcarbonyl)amino]oxoacetyl]amino]-2-thienylacetyl]amino]-3-[[(1-methyl-1H-tetrazol-5-yl)thio]methyl]-8-oxo-5-thia-1-azabicyclo[4.2.0]-oct-2-ene-2-carboxylic acid is obtained as a beige powder which is reprecipitated from tetrahydrofuran/ether, m.p. 156°.

EXAMPLE 11

7-[[D-[[[(2-Furanylcarbonyl)amino]oxoacetyl]amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid, potassium salt The product of Example 10 is reacted with an equimolar aqueous solution of potassium bicarbonate to obtain 7-[[D-[[[(2-furanylcarbonyl)amino]oxoacetyl]amino]-2-thienylacetyl]amino-3-[[(1-methyl-1H-tetrazol-5-yl)thio]methyl]-8-oxo-5-thia-1-azabicyclo[4.2.-0]oct-2-ene-2-carboxylic acid, potassium salt as a brownish powder.

EXAMPLES 12-70

Following the procedure of Example 10 but employing the acylating agent A below having the substituents in the following table (which is prepared as described in Examples 1, 2, 5 and 7) and the 7β-aminocephalosporanic acid Compound B below, one obtains the product C having the same substituents shown in the table. The salts are produced as in Example 11.

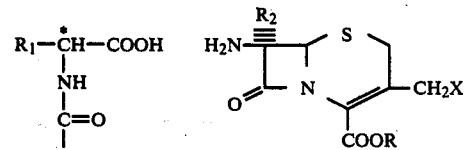

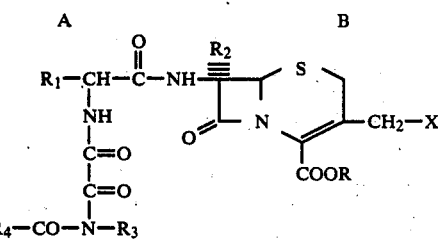

| Ex. | $R_1$ | $R_2$ | R | $R_3$ | $R_4$ | X |
|---|---|---|---|---|---|---|
| 12 | thiophene | H | t-$C_4H_9$ | H | $CH_3$ | -S-(thiadiazole-CH₃) |
| 13 | thiophene | H | H | H | phenyl | -S-(thiadiazole-CH₃) |
| 14 | thiophene | -$OCH_3$ | -$CH_2$-phenyl | H | pyridyl | -S-(tetrazole-N-CH₃) |

-continued

| Ex. | R₁ | R₂ | R | R₃ | R₄ | X |
|---|---|---|---|---|---|---|
| 15 | thienyl | —OCH₃ | H | H | thiazolyl | —S-(1-methyl-tetrazol-5-yl) |
| 16 | phenyl | H | —CH(C₆H₅)₂ | CH₃ | CH₃ | —S-(1-methyl-tetrazol-5-yl) |
| 17 | phenyl | —OCH₃ | H | H | cyclohexyl | —S-(1-methyl-tetrazol-5-yl) |
| 18 | thienyl | H | —CH₂CCl₃ | C₂H₅ | cyclopentyl | —S-(1-ethyl-tetrazol-5-yl) |
| 19 | thienyl | H | CH₃ | H | thienyl | —S-(pyridine N-oxide) |
| 20 | phenyl | H | Na | H | furyl | —S-(pyridine N-oxide) |
| 21 | phenyl | —OCH₃ | —CH(C₆H₅)₂ | C₂H₅ | C₂H₅ | —S-(1-methyl-tetrazol-5-yl) |
| 22 | piperidyl | H | H | H | pyridyl | —S-(1-methyl-tetrazol-5-yl) |
| 23 | thienyl | H | H | H | furyl | —O—C(=O)—CH₃ |
| 24 | furyl | —OCH₃ | —C₂H₅ | —CH₃ | CH₃ | —S-(1-methyl-tetrazol-5-yl) |
| 25 | furyl | H | H | H | 2,4-dichlorophenyl | —O—C(=O)—CH₃ |
| 26 | phenyl | H | H | C₂H₅ | 4-methoxyphenyl | —S—CH₃ |
| 27 | phenyl | —OCH₃ | H | H | 3,5-dimethylphenyl | —CONH₂ |

-continued
| Ex. | R₁ | R₂ | R | R₃ | R₄ | X |
|---|---|---|---|---|---|---|
| 28 |  | H | H | H | 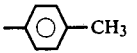—CH₃ | 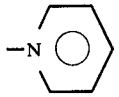 |
| 29 |  | —OCH₃ | H | H | 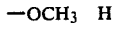 |  |
| 30 | 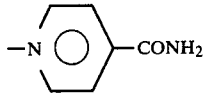 | H | K | H | —Br | 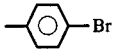 |
| 31 | 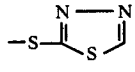 | H | -t-C₄H₉ | —CH₃ | 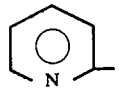 | —OCH₃ |
| 32 |  | H | —CH(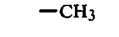)₂ | H |  |  |
| 33 | 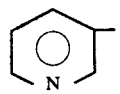 | H | K | —CH₂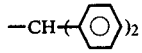 | CH₃ |  |
| 34 | H | H | —(CH₂)₂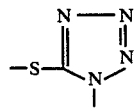 | H |  | 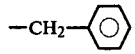 |
| 35 | —C₂H₅ | —OCH₃ | t-C₄H₉ | C₃H₇ | 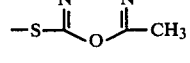 | 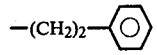 |
| 36 |  | H | —N(C₂H₅)₃ | H | 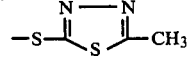 | H |
| 37 |  | H | H | H |  | —S—CH₃ |
| 38 | 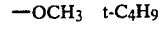 | H | —CH(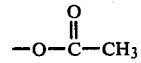)₂ | H |  | 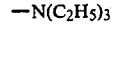 |
| 39 |  | —OCH₃ | H | H |  | —OCH₃ |
| 40 | 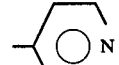 | H | —CH(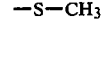)₂ | CH₃ | CH₃ |  |
| 41 | 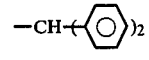 | —OCH₃ | H | H |  | 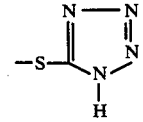 |
| 42 |  | H | —CH()₂ | H |  |  |
| 43 |  | —OCH₃ | H | H | 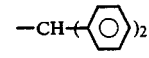 | H |
| 44 | 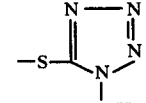 | H | K | —CH₂ | CH₃ |  |

-continued
| Ex. | R₁ | R₂ | R | R₃ | R₄ | X |
|---|---|---|---|---|---|---|
| 45 |  | H | H | —(CH₂)₂— |  | H |
| 46 |  | H | -t-C₄H₉ | H | C₂H₅ | 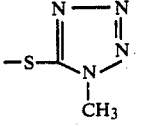 |
| 47 | 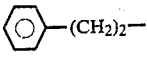—(CH₂)₂— | H | H | H |  | 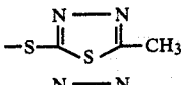 |
| 48 |  | H | H | CH₃ | CH₃ | 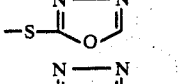 |
| 49 |  | —OCH₃ | H | H | 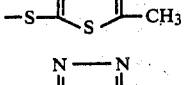 |  |
| 50 |  | H | —CH(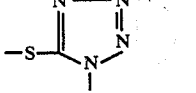)₂ | H | CH₃ |  |
| 51 | HO— | H | —CH(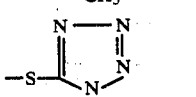)₂ | H | CH₃ | 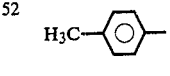 |
| 52 | H₃C— | H | —CH₂—CCl₃ | CH₃ | 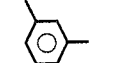 |  |
| 53 |  | H | —CH(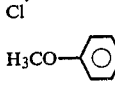)₂ | H |  |  |
| 54 | H₃CO— | H | H | H | 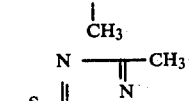 |  |
| 55 |  | H | —CH()₂ | H | CH₃ |  |
| 56 | 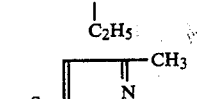 | —OCH₃ | —CH₂—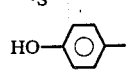 | CH₃ |  |  |
| 57 | 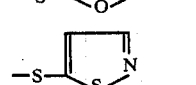 | H | H | CH₃ |  |  |
| 58 | HO—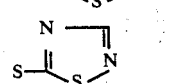 | H | H | H |  |  |
| 59 |  | H | H | H | 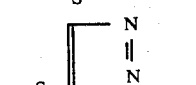—OH |  |
| 60 |  | H | Na | H |  |  |
| 61 |  | H | H | CH₂— |  |  |

-continued

| Ex. | R₁ | R₂ | R | R₃ | R₄ | X |
|---|---|---|---|---|---|---|
| 62 | phenyl | H | H | H | CH₃ | —S—C₂H₅ |
| 63 | phenyl | —OCH₃ | Si(CH₃)₃ | H | CH₃ | —S-(1-methyl-tetrazolyl) |
| 64 | 2-aminothiazol-4-yl | H | H | H | 2-thienyl | —S-(1-methyl-tetrazolyl) |
| 65 | 2-aminothiazol-4-yl | —OCH₃ | H | H | 2-furyl | —S-(1-methyl-tetrazolyl) |
| 66 | 2-aminothiazol-4-yl | H | H | H | 2-thienyl | —OCOCH₃ |
| 67 | 2-aminothiazol-4-yl | H | Na | H | CH₃ | H |
| 68 | H | H | H | H | 2-furyl | —S-(1-methyl-tetrazolyl) |
| 69 | H | H | H | H | 2-thienyl | —OCOCH₃ |
| 70 | H | OCH₃ | H | H | 2-furyl | H |

The acylating agents A may be in either the D- or L-form or may be a mixture of D- and L-isomers.

What is claimed is:

1. A compound of the formula

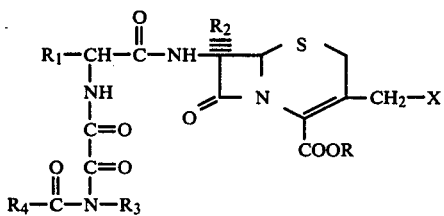

wherein R is hydrogen, lower alkyl, phenyl-lower alkyl, diphenyl-lower alkyl, tri(lower alkyl)silyl, trihaloethyl, aluminum, alkali metal, alkaline earth metal, phenyl-lower alkylamine, N,N-dibenzylethylenediamine, lower alkylamines, triethylamine, or N-lower alkylpiperidines; R₁ is hydrogen, lower alkyl, saturated or unsaturated cycloalkyl of up to 7 carbons, phenyl, phenyl-lower alkyl, substituted phenyl wherein said phenyl substituent is one or two members selected from the group consisting of halogen, lower alkyl, lower alkoxy, and hydroxy, or a heterocyclic selected from the group consisting of 2-thienyl, 3-thienyl, 2-furyl, 3-furyl, 2-pyridyl, 3-pyridyl, 4-pyridyl and 2-aminothiazolyl; R₂ is hydrogen or methoxy; R₃ is hydrogen, lower alkyl or phenyl-lower alkyl; R₄ is lower alkyl, cycloalkyl of up to 7 carbons, phenyl, substituted phenyl wherein the phenyl substituent is as defined above, or a heterocyclic selected from the group consisting of thienyl, furyl, pyridyl, thiazolyl and isothiazolyl; and X is hydrogen, lower alkanoyloxy,

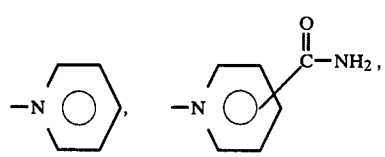

carbamoyloxy, lower alkoxy, lower alkylthio, or a heterothio group selected from the group consisting of

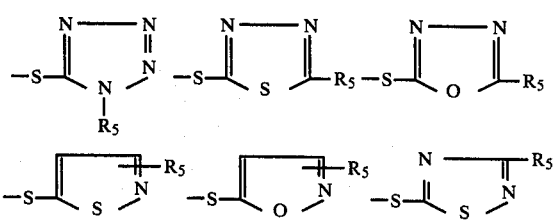

-continued

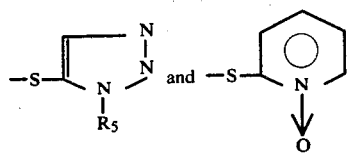

and $R_5$ is hydrogen or lower alkyl.

2. A compound as in claim 1 wherein $R_1$ is thienyl.
3. A compound as in claim 1 wherein $R_1$ is phenyl.
4. A compound as in claim 1 wherein X is methyltetrazolyl.
5. A compound as in claim 1 wherein R, $R_2$ and $R_3$ each is hydrogen.
6. A compound as in claim 1 wherein R is hydrogen or alkali metal; $R_1$ is phenyl, thienyl or furyl; $R_2$ is hydrogen or methoxy; $R_3$ is hydrogen or lower alkyl; $R_4$ is lower alkyl or furyl; and X is as defined in claim 1.
7. A compound as in claim 1 wherein R is hydrogen, sodium or potassium; $R_1$ is phenyl, thienyl or furyl; $R_2$ and $R_3$ each is hydrogen; $R_4$ is furyl; and X is acetoxy or (1-methyl-1H-tetrazol-5-yl)thio.
8. A compound as in claim 1 wherein R, $R_2$ and $R_3$ each is hydrogen, $R_1$ is 2-thienyl; $R_4$ is 2-furyl; and X is (1-methyl-1H-tetrazol-5-yl)thio.
9. A compound as in claim 1 wherein R is alkali metal; $R_2$ and $R_3$ each is hydrogen; $R_1$ is 2-thienyl; $R_4$ is 2-furyl; and X is (1-methyl-1H-tetrazol-5-yl)thio.
10. A compound as in claim 1 wherein R, $R_2$ and $R_3$ each is hydrogen; $R_1$ and $R_4$ each is 2-furyl; and X is (1-methyl-1H-tetrazol-5-yl)thio.

* * * * *

UNITED STATES PATENT AND TRADEMARK OFFICE
CERTIFICATE OF CORRECTION

PATENT NO. : 4,169,947
DATED : October 2, 1979
INVENTOR(S) : Uwe D. Treuner et al.

It is certified that error appears in the above-identified patent and that said Letters Patent are hereby corrected as shown below:

Column 1, line 10, "7β-(2" should read --7β-[(2--.
Column 3, line 63, "formula II" should read --formula III--.
Column 12, Ex. 27, Column X should read -- -OCONH$_2$ --.

Signed and Sealed this

Twelfth Day of February 1980

[SEAL]

Attest:

SIDNEY A. DIAMOND

Attesting Officer

Commissioner of Patents and Trademarks